(12) United States Patent
Perry

(10) Patent No.: US 8,141,711 B2
(45) Date of Patent: Mar. 27, 2012

(54) HYGIENE PRODUCT ASSEMBLY AND METHOD

(76) Inventor: Gwendolyn F. Perry, Flossmoor, IL (US)

( * ) Notice: Subject to any disclaimer, the term of this patent is extended or adjusted under 35 U.S.C. 154(b) by 0 days.

(21) Appl. No.: 12/815,139

(22) Filed: Jun. 14, 2010

(65) Prior Publication Data

US 2010/0320115 A1 Dec. 23, 2010

Related U.S. Application Data

(60) Provisional application No. 61/187,803, filed on Jun. 17, 2009.

(51) Int. Cl.
*A61F 13/20* (2006.01)
*A61B 19/02* (2006.01)
(52) U.S. Cl. .............. 206/581; 206/440; 604/385.02
(58) Field of Classification Search ........... 206/581, 206/440, 438, 38, 216; 604/904, 15, 358, 604/385.02, 385.06, 359; 53/461
See application file for complete search history.

(56) References Cited

U.S. PATENT DOCUMENTS

| | | | |
|---|---|---|---|
| 4,332,319 A * | 6/1982 | Hurwood | 206/210 |
| 4,790,840 A * | 12/1988 | Cortina | 604/385.06 |
| 4,881,644 A * | 11/1989 | Norquest et al. | 206/363 |
| 5,261,531 A | 11/1993 | Nieves | |
| 5,569,230 A | 10/1996 | Fisher et al. | |
| 5,964,741 A * | 10/1999 | Moder et al. | 604/358 |
| 5,986,165 A | 11/1999 | Moder et al. | |
| 5,988,386 A | 11/1999 | Morrow | |
| D448,479 S * | 9/2001 | Foy | D24/125 |
| 6,350,931 B1 | 2/2002 | Martin | |
| 6,911,022 B2 * | 6/2005 | Steger et al. | 604/385.05 |
| 6,994,696 B2 * | 2/2006 | Suga | 604/385.02 |
| 7,144,391 B1 * | 12/2006 | Kreutz et al. | 604/385.17 |
| D619,478 S * | 7/2010 | Drewnowski et al. | D9/707 |
| 2004/0112779 A1 * | 6/2004 | Arndt | 206/363 |
| 2007/0142811 A1 * | 6/2007 | Lais | 604/385.06 |
| 2008/0027405 A1 * | 1/2008 | Hernandez et al. | 604/385.06 |
| 2008/0269708 A1 * | 10/2008 | Caracci et al. | 604/385.02 |
| 2009/0112148 A1 | 4/2009 | Morrow | |
| 2009/0112174 A1 * | 4/2009 | Drevik et al. | 604/385.02 |

* cited by examiner

*Primary Examiner* — Steven A. Reynolds
(74) *Attorney, Agent, or Firm* — Barnes & Thornburg LLP

(57) ABSTRACT

A personal hygiene assembly including a personal hygiene article such as a tampon and a towelette. The tampon is individually packaged in a wrapper and the towelette is also individually packaged in a wrapper. The assembly attaches the towelette package to the tampon package for convenient co-location of the articles. The towelette package can be attached to the outside surface of the tampon package either after sealing of the tampon package or during the sealing of the tampon package. As both the tampon package and the towelette package have a generally linear axial orientation, the articles can be axially aligned for attachment and convenient storage.

20 Claims, 5 Drawing Sheets

HYGIENE PRODUCT ASSEMBLY AND METHOD

CROSS-REFERENCE TO RELATED APPLICATIONS

This application claims priority to U.S. Provisional Application No. 61/187,803 filed Jun. 17, 2009 the entire application of which is incorporated by reference in the entirety. The disclosure set forth in the referenced application is incorporated herein by reference in its entirety, including all information as originally submitted to the United States Patent and Trademark Office.

BACKGROUND

The present disclosure relates to feminine hygiene products packaged individually and in combination with individually packaged cleaning products to provide a convenient personal hygiene product assembly.

By way of background, a variety of feminine hygiene products have been provided in convenient individual single use packaging. Such feminine hygiene products may include tampons, sanitary napkins, panty liners and other variations of such products. The convenience packaging is useful to allow a user to have the necessary items available when needed. This is particularly useful for packaging and carrying in a user's purse, pocket, briefcase, backpack or other area.

When the need for a feminine hygiene product arises, manufacturers have made access to the specific product convenient as noted above. However, after using the product and disposing of a prior product, it may be necessary to clean up after use. In this regard, after use of a tampon, excess fluids, such as blood, may be left behind on the user's fingers and hands. This can make it difficult to pull up their undergarment, realign clothing and may cause embarrassing stains.

Also, when one touches various surfaces, bathroom door, door handles, faucet handles, etc. blood-borne pathogens may be transmitted to the surface. This may allow viruses or other ailments to be contracted after another person uses those surfaces. One may feel uncomfortable being seen exiting a public bathroom or stall with blood remaining on their hand. While public restrooms will have tissue available, tissue may not sufficiently remove the remaining fluids. Having a simple and easily accessible way for one to cleanse their hands after use of a tampon and before exiting a bathroom stall, will assist individuals in having a more comfortable and secure experience using feminine hygiene products.

The present disclosure discloses a single use individually packaged feminine hygiene product which includes an individually packaged single use moist towelette which is attached to the single use individually packaged feminine hygiene product. The combination hygiene product and moist towelette packaging permits a user to have a unitary item which could be selected and stored for later use. The use of a unitary product allows a user the piece of mind of having the necessary items with them at all times.

The exemplifications set out herein illustrate embodiments of the disclosure that are not to be construed as limiting the scope of the disclosure in any manner. Additional features of the present disclosure will become apparent to those skilled in the art upon consideration of the following detailed description exemplifying at least the best mode of carrying out the disclosure as presently perceived.

DETAILED DESCRIPTION

Figure 1:
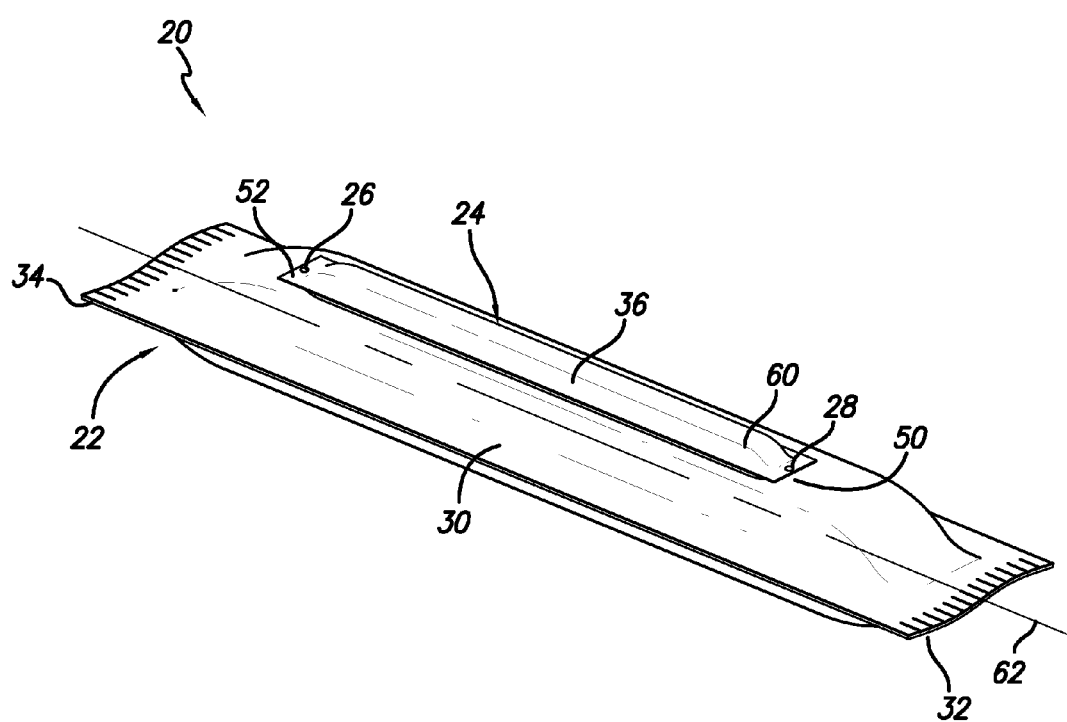
FIG. 1 is a perspective view of a personal assembly including a single use individually wrapped feminine hygiene product package and a single use individually wrapped towelette package attached to the hygiene product, the assembly providing a single use unitary packaging article.
Figure 2:
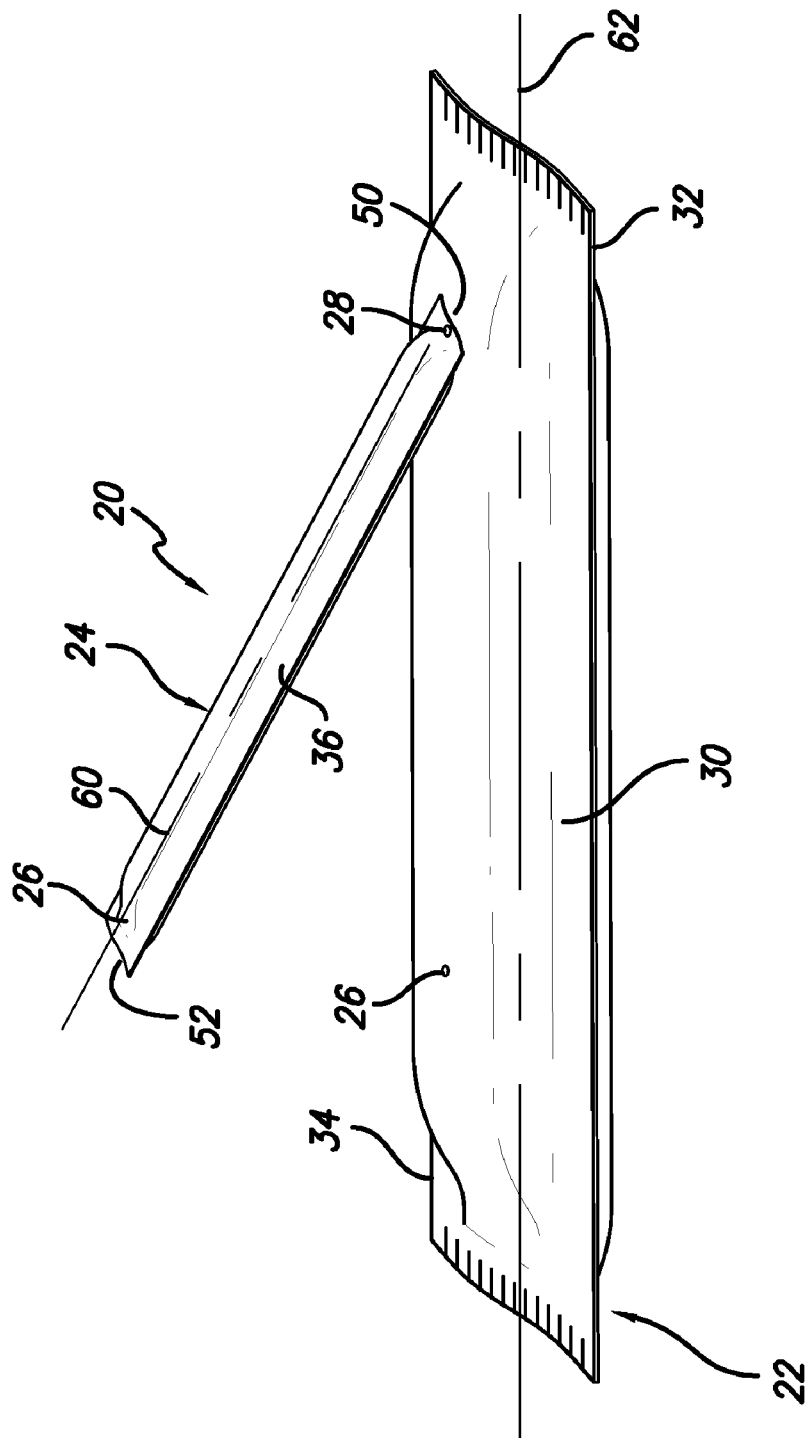
FIG. 2 is a view of the personal hygiene product assembly as shown in FIG. 1 in which the towelette package has been removed at one end from the outside surface of the hygiene product package for removal during use.
Figure 3:
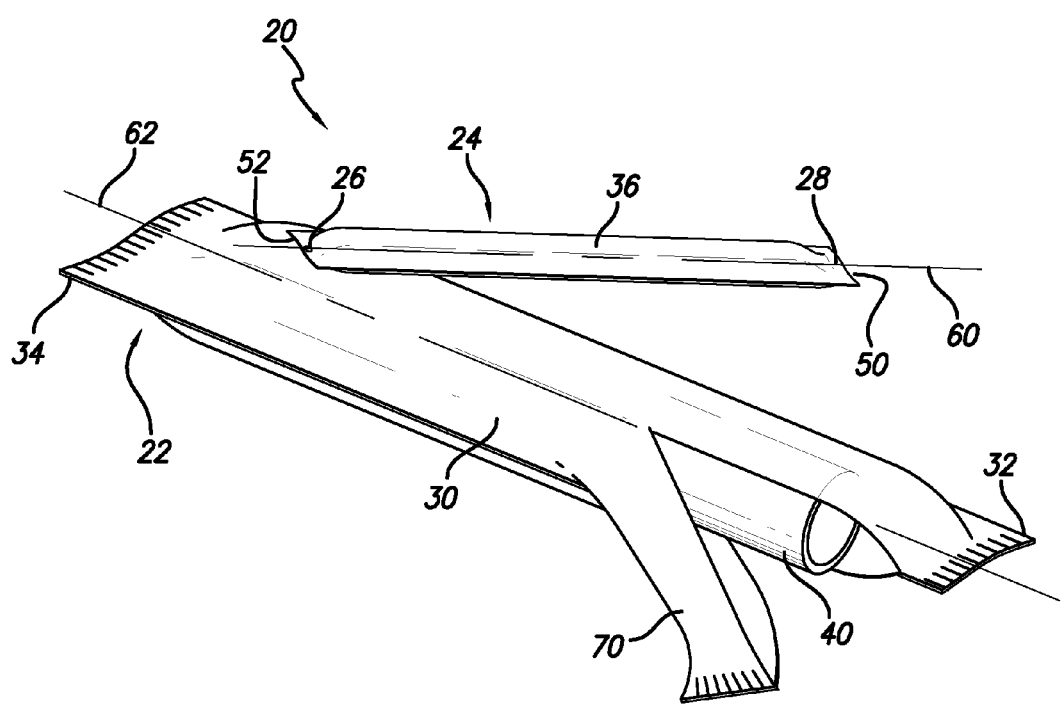
FIG. 3 is another step in the progression of use, continuing from FIG. 2, in which a feminine hygiene is packaged, in this case a tampon, in which the wrapper covering the tampon has been opened for removal of the tampon from the wrapper.

While the present disclosure may be susceptible to embodiment in different forms, there is shown in the drawings, and herein will be described in detail, embodiments with the understanding that the present description is to be considered an exemplification of the principles of the disclosure and is not intended to be exhaustive or to limit the disclosure to the details of construction and the arrangements of components set forth in the following description or as illustrated in the drawings.

The user of the disclosed articles will be familiar with use of the articles from prior use of similar articles. The disclosure includes a hygiene product being produced and provided as a hygiene assembly package article 20. The assembly 20 includes a hygiene product 22 with a towelette package 24 attached 26, 28 to the hygiene product package 22. Multiple assemblies 20 may be packaged in common box for sale or the assemblies 20 may be sold individually, such as in a bathroom, stall, or other convenience setting.

Figure 4:
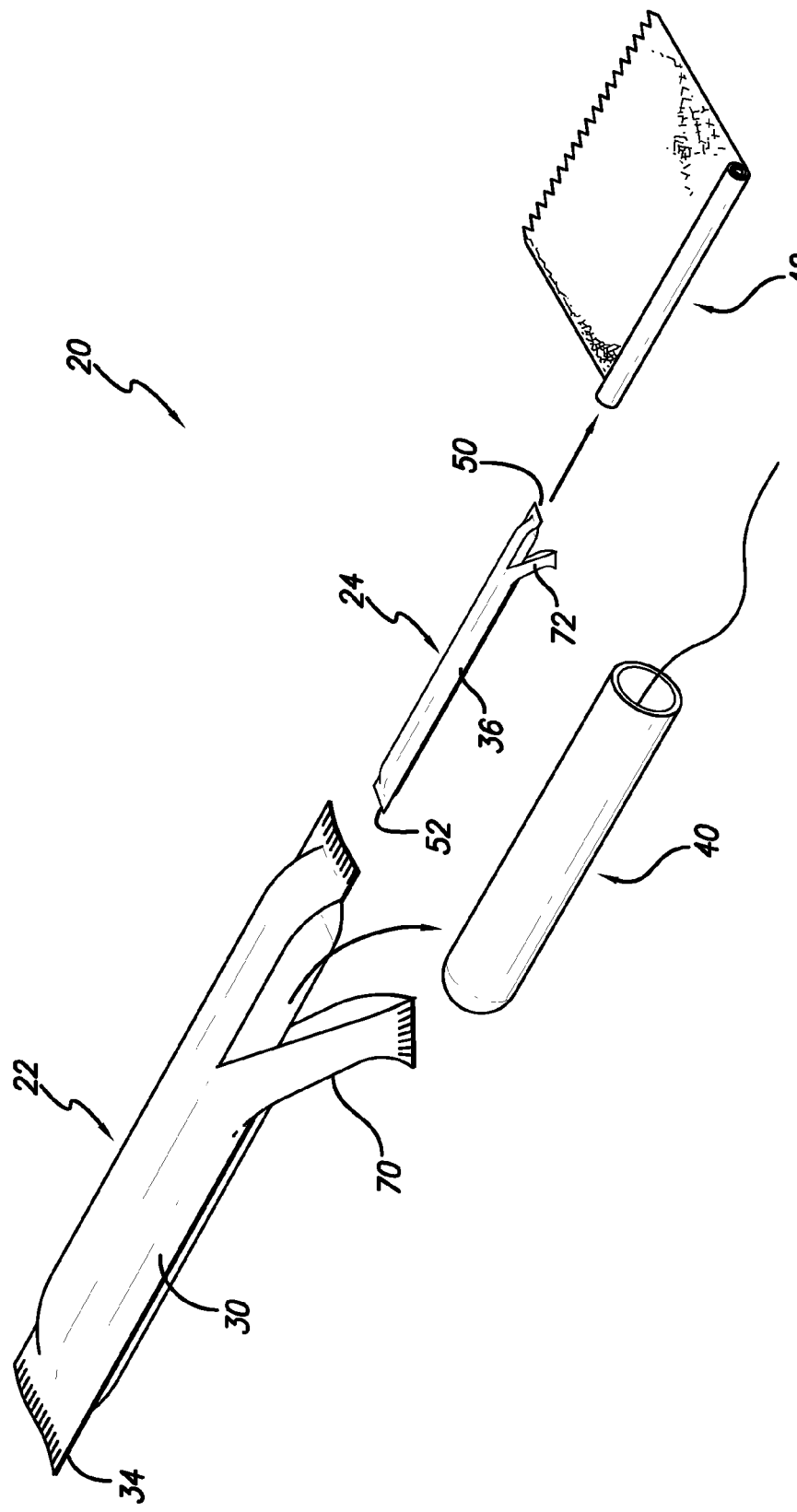
FIG. 4 is an exploded view of the personal hygiene assembly showing the wrapper of the hygiene product package being opened with the tampon therein being removed, also showing a wrapper of the towelette package having been opened and the towelette being removed therefrom, further showing the moist towelette being unrolled for use.

It should be noted that a feminine hygiene product 40 (see FIG. 4) may be any one of a variety of such products which are currently known or hereafter developed which includes, by way of illustration and not limitation: tampons, pads, sanitary napkins, panty liners and other such articles. For convenience in the present disclosure these items are collectively referred to as a tampon although it is understood that a variety of articles having a variety of purposes and a variety of designs using a variety of materials may be included. The use of the term tampon is merely used as an expedient and is in no way intended to limit these articles.

Similarly, while a towelette is referred to, it is possible that a variety of other cleansing products may be used in conjunction with the individually packaged tampons. In this regard, the towelette is referred to by way of illustration and not limitation. In this regard, it may be desirable to include a moist towelette, tissue, cloth, absorbent materials or a variety of other products which may be used to clean up after the use of the tampon. While reference to a towelette is used throughout this application as an expedient, the towelette need not be moist. Additionally, while the towelette is shown as being rolled, it is possible that a variety of other packaging configurations can be achieved using such a towelette while providing the benefits of attachment to the assembly 20 as described herein. The use of a rolled towelette is one version of an embodiment set forth in the present disclosure and is provided by way of illustration and not limitation.

The individually packaged and sealed tampon is widely and conveniently produced in mass quantities. This type of packaging may be formed of a tubular wrapper which is cut to length and sealed or sealed and cut to length. The towelette may be packaged using the same tubular wrapper packaging technology and process. The individual towelette package can be attached to the outside of the tampon package using a variety of attachment techniques and methods. While several techniques are disclosed herein, the techniques are in no way intended to be limiting and are instead referred to provide illustrations of attaching an individually packaged towelette to an individually packaged tampon. Attachment may occur by use of adhesives, radio frequency welding, ultrasonic welding, heat staking, pressure bonding or any other technique which will sufficiently attach the individually packaged towelette to the individually packaged tampon.

The materials used for the tampon, packaging for the tampon as well as the towelette and packaging for the towelette may incorporate various desirable characteristics which may include degradability sufficient to allow the products to be flushable. One or more of the components as described may have such characteristics. Additionally, some or all of the components may also include other desirable characteristics such as anti-microbial, antibacterial, or antibiotic treatments, surfaces, coatings or other characteristics. The components may also be provided with fragrance or deodorizing characteristics to provide a more discreet and pleasant experience. The wrapper material may be provided of a material which can be readily torn by a user without tools for removal of the article from the wrapper. The feminine hygiene product and towelette may also be provided in a variety of sizes to accommodate different user's preferences and needs. For example, the tampons may provide in levels such as regular, super or super plus based on a particular manufacturer's grading or industry system. Similarly, the towelette may be provided in a variety of sizes which might be deemed appropriate with the corresponding tampon and after further refinement based on user's preferences.

According to FIG. 1, the single use individually wrapped feminine hygiene product package 22 is shown in a wrapper 30 having a first end 32 and a second end 34 which are sealed. Similarly, the individually wrapped towelette package 24 is shown in a wrapper 36 having a first end 50 and a second end 52. The attachments 26, 28 allow the towelette package 24 to be sufficiently attached to the hygiene product package 22 to be carried as an assembly 20. The towelette package 24 is easily removed from the tampon package 22 by applying sufficient pressure to break the attachment 26, 28. This is a quick and simple operation which is helpful if the product is used with some urgency. As such, the towelette package 24 is generally attached in a manner which generally aligns a central access axis 60 of the towelette package with a corresponding central axis 62 of the tampon package 22. The coaxial alignment (60, 62) of these two (22, 24) generally elongated articles allows for convenient assembly of the articles during a manufacturing process.

Figure 5:
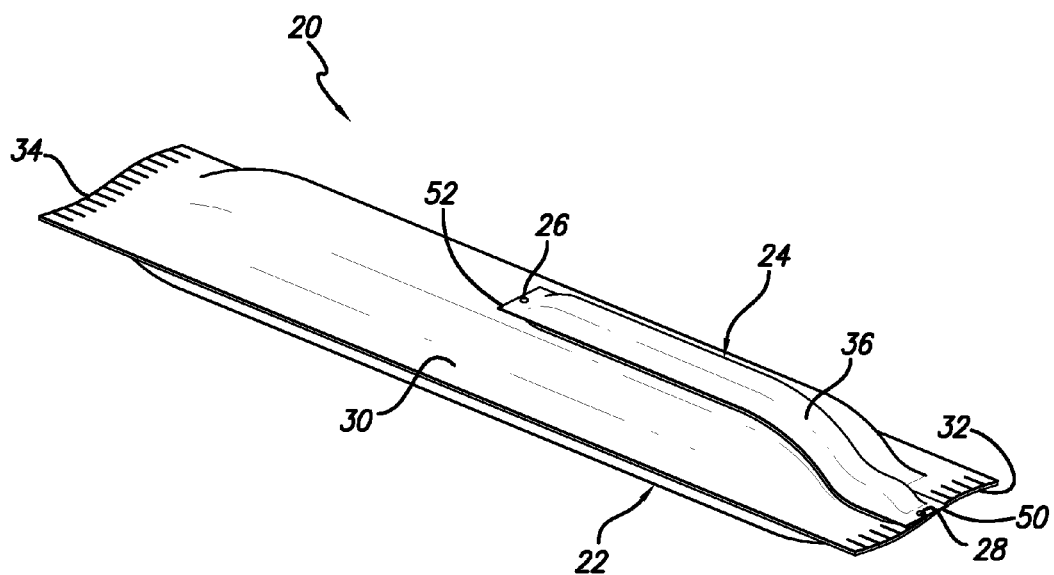
FIG. 5 is an alternate embodiment showing the towelette package attached at one end and to a first sealed end of the hygiene product package and attached at a second end to the outside surface of the hygiene product package wrapper.
Figure 6:
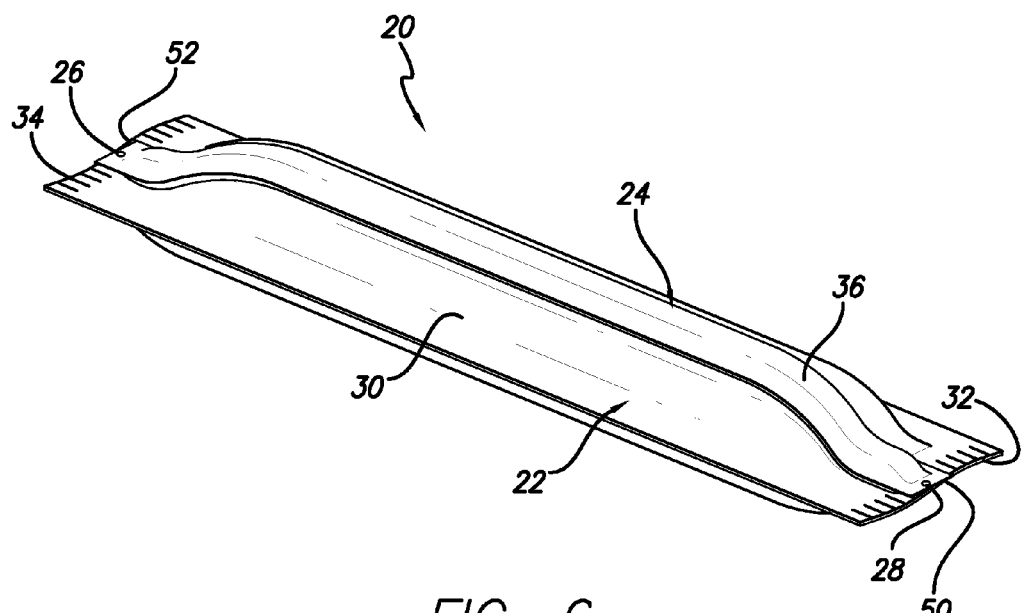
FIG. 6 is another embodiment of the personal hygiene assembly showing a first end of the towelette package attached to the first sealed end of the hygiene product and a second end of the towelette package attached to a second sealed end of the hygiene product packaging, this embodiment allowing the towelette package to be attached in a process line using the same systems used to seal the first and second ends of the hygiene product package.

With regard to the manufacturability of this assembly 20, we refer to FIGS. 1, 5 and 6. In this regard, tampon packages 22 are of known constructions. Generally, the first end 32 and the second end 34 are sealed with an adhesive, heating, or other known system for sealing these ends. A similar system can be used to seal the first and second ends 26, 28 of the towelette package 24. In such a process, the two packages 22, 24 can be brought together during an assembly process and attach the towelette package 22 to the tampon package 24. This can be accomplished using adhesive applied between corresponding portions of the towelette 24 package and the product package 22. Controlled heating may be applied to at least one portion of the towelette package 22 and a corresponding portion of the product package 24 forming a heated area (for example 26, 28) of the wrappers 30, 36. Similarly, controlled application of non-heat energy such as RF or ultrasonic energy may be applied to at least one portion of the towelette package 22 and a corresponding portion of the product package 24 forming a bonded or attached area (for example 26, 28) of the wrappers 30, 36.

With reference to FIGS. 5 and 6, additionally efficiency might be achieved if a first end 28 of the towelette package 24 is attached during the manufacturing operation of sealing the first end 32 of the tampon package 22. This would allow the second end 26 of the towelette package 22 to be attached to the outside surface or wrapper 30 of the tampon package 22. Similarly, the first end 28 and the second end 26 of the towelette package 24 can be attached to the corresponding first end 32 and second end 34 of the tampon package 32. As shown in FIG. 6, the two generally axially aligned packages, 22 and 24, can be coordinated in the manufacturing process so that the corresponding first ends (28, 32) and second end (26, 34) can be attached and/or sealed at the same time. It may be preferable to seal the towelette package 24 prior to the tampon package 22, especially if it is a pre-moistened towelette. It may also be preferable to assemble the sealed towelette package 24 to the tampon package 22 as it is being sealed at the first end 32 and the second end 34. Regardless of the technique used, this present disclosure utilizes various manufacturing processes and combinations to more efficiently and cost effectively manufacture a hygiene product assembly 20.

In use, a user will take the package as shown in FIG. 1, 5 or 6 and place it in a convenient location such as a purse, bag or cabinet for subsequent use. When the need arises, the user will take the assembly 20 and either open the wrapper 70 of the tampon package 22 for removal of the tampon 40 or remove the towelette package 24. The actual specific steps used in opening the packages may be a personal preference. Nevertheless, necessary items, the tampon 40 and the towelette 42 will be conveniently available and individually packaged in sanitary wrappers for use by the individual. Once the wrapper 70 of the tampon package 22 has been opened, the tampon 40 can be used in a customary manner. Similarly, the towelette package 22 can remain attached to the wrapper 70 of the tampon package 22 or may be individually removed for convenient placement and subsequent use. At the appropriate time, a wrapper 72 of the towelette package 22 can be opened for removal of the towelette 42. The towelette 42 can be opened for use either by unrolling or any other appropriate method. Typically, the two packages 22, 24 will be of different sizes which will provide visual clues to the user in choosing which package to open at which time during the use process. The single assembly 20 provides convenience and flexibility for a user to know that they have two essential components of this necessary personal hygiene activity.

After insertion of the tampon 40 and use of the towelette 42 the remaining part of the applicator and packaging can be disposed of in a waste receptacle or, depending on the manufacturing of this article, flushed if provided with a degradable material.

While this disclosure has been described as having an exemplary embodiment, this application is intended to cover any variations, uses, or adaptations using its general principles. It is envisioned that those skilled in the art may devise various modifications and equivalents without departing from the spirit and scope of the disclosure as recited in the following claims. Further, this application is intended to cover such departures from the present disclosure as come within the known or customary practice within the art to which it pertains.

The invention claimed is:

1. A personal hygiene assembly comprising:
   an individually wrapped personal hygiene product package having an openable hygiene wrapper containing a removable tampon, the openable hygiene wrapper having at least a first sealed end and a second sealed end, thereby providing the removable tampon in a sealed hygiene product wrapper, the first and second sealed ends of the openable hygiene wrapper defining spaced apart ends of a primary hygiene product axis and being openable for removal of the tampon from the openable hygiene wrapper for use by a user;
   an individually wrapped towelette package having a towelette wrapper containing a towelette in an axially elongated condition, the towelette wrapper having at least a first sealed end and a second sealed end, thereby providing the towelette in a sealed towelette wrapper, the first and second sealed ends of the towelette package defining spaced apart ends of a primary towelette axis; and
   an exterior portion of the towelette wrapper being attached to an exterior portion of the hygiene wrapper for generally co-axial attachment of the towelette package on the hygiene product package with the sealed towelette wrapper being entirely on one side of the sealed openable hygiene wrapper and whereby the sealed towelette wrapper is easily removed from the openable hygiene wrapper by breaking the attachment of the towelette and hygiene wrappers.

2. The personal hygiene assembly of claim 1, wherein the exterior portion of the towelette wrapper is attached to an exterior portion of the hygiene wrapper at only two spaced locations on the one side of the exterior of the hygiene product wrapper.

3. The personal hygiene assembly of claim 2, wherein the two spaced locations are a first location at the first sealed end of the hygiene wrapper attached to the first sealed end of the towelette wrapper and a second location at the second sealed end of the hygiene wrapper attached to the second sealed end of the towelette wrapper.

4. The personal hygiene assembly of claim 1, wherein the first sealed end of the towelette wrapper is attached to the first sealed end of the hygiene product wrapper and the towelette wrapper and the hygiene product wrapper are not attached at any other location.

5. The personal hygiene assembly of claim 1, wherein the sealed towelette wrapper is attached to an outside surface of the sealed hygiene product wrapper at only one location on the one side of the sealed openable hygiene product wrapper.

6. The personal hygiene assembly of claim 1, wherein the towelette is wrapped round and round onto itself into a rolled configuration within the towelette wrapper.

7. The personal hygiene assembly of claim 1, further comprising: the towelette is a pre-moistened towelette.

8. The personal hygiene assembly of claim 1, further comprising: antimicrobial substance applied to the towelette.

9. The personal hygiene assembly of claim 1, further comprising: antibacterial substance applied to the towelette.

10. The personal hygiene assembly of claim 1, further comprising: fragrance applied to the towelette.

11. The personal hygiene assembly of claim 1, further comprising: the hygiene product wrapper formed of a material that can be torn by a user without tools for removal of the tampon therefrom.

12. The personal hygiene assembly of claim 1, further comprising: the towelette wrapper formed of a material that can be torn by a user without tools for removal of the towelette therefrom.

13. The personal hygiene assembly of claim 1, further comprising: adhesive applied between the towelette package and the hygiene product package for attaching the towelette package to the hygiene product package.

14. The personal hygiene assembly of claim 1, further comprising: applying heat to at least one portion of the towelette package and to a corresponding portion of the hygiene product package forming a heated attached area of the towelette wrapper and the hygiene wrapper.

15. The personal hygiene assembly of claim 1, further comprising: applying non-heat energy to at least one portion of the towelette package and to a corresponding portion of the hygiene product package forming an energy attached area of the towelette wrapper and the personal hygiene wrapper.

16. A method of making a personal hygiene assembly comprising the steps of:
   providing an individually sealed tampon by individually wrapping an axially elongated removable tampon in a hygiene product wrapper defining a hygiene product package with a tampon that is removable for use by a user;
   sealing a first end of the hygiene product wrapper; and
   sealing a second end of the hygiene product wrapper to provide the removable tampon in a sealed hygiene product wrapper;
   providing an individually sealed towelette by individually wrapping an axially elongated towelette in a towelette wrapper defining a towelette package;
   sealing a first end of the towelette wrapper; and
   sealing a second end of the towelette wrapper to provide the towelette in a sealed towelette wrapper; and
   attaching an exterior portion of the sealed towelette wrapper to an exterior portion of the sealed hygiene product wrapper for generally co-axial attachment of the sealed towelette package on the sealed hygiene product package so that the sealed towelette wrapper is entirely on one side of the sealed hygiene product package whereby the sealed towelette wrapper is easily removed from the sealed hygiene product package by breaking the attachment of the exterior portions.

17. The method of claim 16, wherein the step of attaching comprises:
   attaching at least one of the first or second ends of the towelette wrapper to one of the first or second ends of the hygiene product wrapper.

18. The method of claim 17, wherein the steps of attaching comprise:
   attaching at least one of the first or second ends of the towelette wrapper to one of the first or second ends of the hygiene product wrapper; and
   attaching the other of the first or second end of the towelette wrapper to an outside of the hygiene product wrapper at a location spaced from the corresponding end of the hygiene wrapper with no attachment between the one of the first or second ends and the location spaced from the corresponding end.

19. The method of claim 16, wherein the steps of attaching comprise:
attaching the first end of the towelette wrapper to the first end of the hygiene product wrapper; and
attaching the second end of the towelette wrapper to the second end of the hygiene product wrapper.

20. The method of claim 16, wherein the step of attaching comprises:
attaching the first end of the towelette wrapper to an outside surface of the hygiene product wrapper at a first location spaced from the first end of the hygiene wrapper; and
attaching the second end of the towelette wrapper to the outside surface of the hygiene product wrapper at a second location spaced from the second end of the hygiene product wrapper with no attachment between the first location and the second location.

* * * * *